US012558552B2

(12) United States Patent
McIntosh et al.

(10) Patent No.: US 12,558,552 B2
(45) Date of Patent: Feb. 24, 2026

(54) THERMAL DOSE CALCULATION AND PROTECTION IN AN IMPLANTABLE MEDICAL DEVICE

(71) Applicant: BIOTRONIK SE & Co. KG, Berlin (DE)

(72) Inventors: David McIntosh, Wilsonville, OR (US); Kai-Oliver Poehlig, West Linn, OR (US); Marcelo Baru, Tualatin, OR (US); Kevin Carl Lu, Happy Valley, OR (US)

(73) Assignee: BIOTRONIK SE & Co. KG, Belin (DE)

( * ) Notice: Subject to any disclaimer, the term of this patent is extended or adjusted under 35 U.S.C. 154(b) by 0 days.

(21) Appl. No.: 19/106,381

(22) PCT Filed: Jul. 19, 2023

(86) PCT No.: PCT/EP2023/070034
§ 371 (c)(1),
(2) Date: Feb. 25, 2025

(87) PCT Pub. No.: WO2024/051994
PCT Pub. Date: Mar. 14, 2024

(65) Prior Publication Data
US 2025/0256109 A1     Aug. 14, 2025

Related U.S. Application Data

(60) Provisional application No. 63/404,430, filed on Sep. 7, 2022.

(30) Foreign Application Priority Data

Oct. 26, 2022     (EP) ..................................... 22203838

(51) Int. Cl.
*A61N 1/372* (2006.01)
*H02J 7/00* (2006.01)

(52) U.S. Cl.
CPC .... *A61N 1/37223* (2013.01); *H02J 7/007188* (2020.01)

(58) Field of Classification Search
CPC ....................... A61N 1/37223; H02J 7/007188
(Continued)

(56) References Cited

U.S. PATENT DOCUMENTS 8,165,693 B2 * 4/2012 Inman ................ A61N 1/36082
607/63
8,165,694 B2 * 4/2012 Carbanaru ............ H02J 7/0042
607/63
(Continued)

OTHER PUBLICATIONS

D. Arora, M. Skliar and R. B. Roemer, "Nonlinear and model predictive control of thermal dose in high temperature therapies," Proceedings of the 2003 American Control Conference, 2003., Denver, CO, USA, 2003, pp. 1200-1205 (Year: 2003).*
(Continued)

*Primary Examiner* — M Baye Diao
(74) *Attorney, Agent, or Firm* — FBT Gibbons LLP

(57) ABSTRACT

A control system (1) is used to control a charging process of an implantable medical device for a patient. The control system (1) includes a means for determining a temperature (10) of a tissue of a patient; and a control unit (20) configured to determine a cumulative thermal dose of the patient based on the determined temperature. The control unit (20) is configured to continue, after an interruption of the charging process and upon resumption of the charging process, the determination of the cumulative thermal dose based on one or more predefined conditions. The control unit (20) is configured to reset the determined cumulative thermal dose when a time span from interruption is greater than (Continued)

Figure 1:
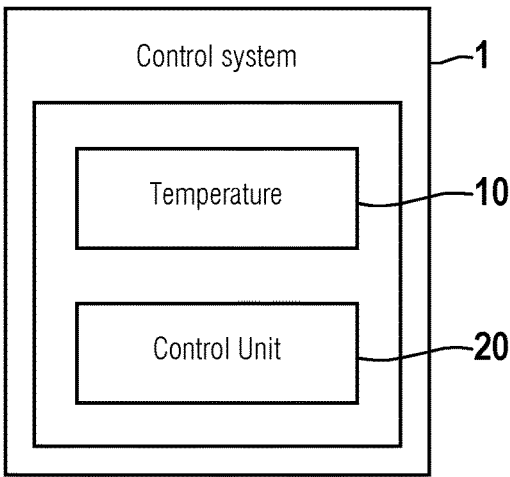

a time limit and/or when a measured temperature is lower than a temperature limit. A method and a corresponding computer program may also provide such control.

20 Claims, 3 Drawing Sheets

(58) Field of Classification Search
USPC ........................................................ 320/137
See application file for complete search history.

(56) References Cited

U.S. PATENT DOCUMENTS

| | | | | | |
|---|---|---|---|---|---|
| 8,321,029 | B2 * | 11/2012 | Aghassian | ......... | A61N 1/37235 |
| | | | | | 607/30 |
| 9,270,134 | B2 * | 2/2016 | Gaddam | ................. | H02J 50/80 |
| 10,112,927 | B2 * | 10/2018 | Gray | ....................... | A61K 45/06 |
| 10,554,069 | B2 * | 2/2020 | Paralikar | ................ | A61B 5/686 |
| 10,682,520 | B2 * | 6/2020 | Kelly | .................... | A61N 1/3787 |
| 10,946,206 | B2 * | 3/2021 | Gaddam | .............. | A61N 1/3787 |
| 2010/0277129 | A1 * | 11/2010 | Long | ................. | H02J 7/007192 |
| | | | | | 320/152 |
| 2011/0071597 | A1 * | 3/2011 | Aghassian | ........... | A61N 1/3787 |
| | | | | | 607/61 |
| 2013/0193914 | A1 | 8/2013 | Gaddam et al. | | |
| 2013/0197613 | A1 | 8/2013 | Kelly et al. | | |
| 2015/0133861 | A1 * | 5/2015 | McLennan | ............... | H05K 7/20 |
| | | | | | 604/113 |

OTHER PUBLICATIONS

International Search Report and Written Opinion dated Sep. 15, 2023, for Application No. PCT/EP2023/070034, 12 pages.

* cited by examiner

1000

Charging ——1100

Determining
temperature ——1200

Determining
thermal dose ——1300

Interruption/Resumption
of determining thermal dose ——1400

THERMAL DOSE CALCULATION AND PROTECTION IN AN IMPLANTABLE MEDICAL DEVICE

The present invention generally relates to a control system for controlling a charging process of an implantable medical device. The present invention is further directed to a system comprising such a control system, to a method and a corresponding computer program.

Medical devices, such as implantable medical devices (IMDs) have gained significant importance in recent years. Examples of IMDs include in a non-exhaustive list pacemakers, defibrillators, pressure sensors, neurostimulators, or the like. Thus, IMDs enjoy a wide range of applications. Furthermore, a demand for IMDs is expected to increase significantly as the value of IMDs is expected to become even more important in the future. Such an increased demand may be fueled by new medical technologies evolving that enable new potentials for IMDs, and this may include medical technologies not deemed realistic as from today's viewpoint.

IMDs usually employ batteries, such as rechargeable batteries. Typically, such batteries require recharging. As an example, a method for recharging may comprise using inductive or resonant magnetic wireless power transfer (WPT). In such a recharging method, eddy currents are usually induced in metal parts of the IMD, such as an Implantable Pulse Generator (IPG), causing the metal parts, the IPG and/or the IMD to heat up. As a consequence, a patient's tissue in proximity to the metal parts, the IPG and/or the IMD is heated up as well. Monitoring an amount of a heat impact or a temperature rise is important for ensuring a patient's health and safety and to avoid risks, discomfort, or an unpleasant feeling associated with overheated tissues.

A potential method for monitoring an amount of a heat impact and/or ensuring safety is CEM43 (cumulative equivalent minutes at 43° C.). A CEM43 of 1 may be equivalent to a temperature exposure of tissue for a single minute at 43° C. In particular, CEM43 may provide a method to equate time-at-a-given-temperature. Usually, a patient's tissue can survive without damage for shorter periods at higher temperatures and longer durations at lower temperatures. Such principle may be reflected by way of CEM43.

As an example, a tissue exposed to a temperature of 41° C. for 10 minutes may represent a CEM43 of 2.5. In another example, a tissue exposed to a temperature of 45° C. for 10 minutes may correspond to a CEM43 of 40.

CEM43 may be calculated to provide for monitoring of an amount of a heat impact of a patient's tissue during a charging process.

However, this approach may not always lead to optimal results. For instance, it stipulates a normal and/or ideal charging process. Such an assumption is obviously flawed and too simplistic. Particularly, realistic circumstances that could lead to a deviation of an ordinary charging process are neglected and not taken into consideration. Accordingly, such conventional devices are not always suited to ensure a patient's health and safety and to avoid risks, discomfort, or an unpleasant feeling associated with overheated tissues during a charging process of an IMD.

In view of the foregoing, there is a need to improve the known approaches for monitoring charging processes of IMDs.

The aspects described herein address the above need at least in part.

A first aspect relates to a control system for controlling a charging process of an implantable medical device, IMD, for a patient. The control system comprises means for determining a temperature of a tissue of a patient. The control system further comprises a control unit configured to determine a cumulative thermal dose of the patient based on the determined temperature. Furthermore, the control unit is configured to continue, after an interruption of the charging process and upon resumption of the charging process, the determination of the cumulative thermal dose based on one or more predefined conditions. The control unit is configured to reset the determined cumulative thermal dose when a time span from interruption is greater than a time limit and/or when a measured temperature is lower than a temperature limit.

The control system may be any system that is suitable for controlling a process such as a charging process. The charging process may be understood as a process that increases an amount of energy (of an element to be charged), such as an electrical or chemical energy or any other type of energy. The energy may be stored in a battery or accumulator. The term accumulator may be understood synonymously to the term battery herein. Preferably this charging process is associated with the charging process of the IMD. An IMD may be used to monitor a patient's condition and/or to deliver therapy to the patient or to perform any different means associated with a health status of the patient. An IMD may comprise a rechargeable power source, such as a battery.

The means for determining a temperature of a tissue of the patient may be any means that are suitable for retrieving a temperature of said tissue. In an example, the means for determining a temperature may be or comprise one or more temperature sensing means, such as one or more temperature sensors. In such an example, determining the temperature of the tissue may comprise measuring the temperature of the tissue. The one or more temperature sensors may be in contact with a tissue of the patient to accurately measure the temperature. In an example, the means for determining a temperature may be part of the IMD to accurately determine a temperature of tissue in proximity to the IMD.

In another example, the means for determining a temperature may (additionally) comprise a (numerical) model, such as a predictive model, and/or a model on a system level to determine the temperature of a tissue of the patient. In such an example, temperature sensors may not necessarily be required. As an example, the temperature could be determined based on a power (or energy) transferred during the charging process of the IMD. Thus, when an increased power is transferred, the model may determine an increased temperature of the patient's tissue and/or vice versa.

As acknowledged, precise determination of the temperature of the tissue may be important since it contributes to increasing the patient's health and/or comfort. As an example, an increased temperature could cause damage to a specific tissue. The evaluation, whether a temperature is increased requires accurate determination of the temperature.

The control unit may determine a cumulative thermal dose of the patient based on the determined temperature. Preferably, the control unit is configured to receive the determined temperature from the means for determining a temperature. This may facilitate a quick and efficient processing by way of the control unit. The cumulative thermal dose, as described herein, may be calculated based on a continuous basis (e.g. continuously or quasi-continuously over a time, e.g. based on periodic temperature measurements and/or an integration of the temperature over time). A thermal dose may be understood as a parameter that describes a heat load. As used herein, the heat load may be associated with a patient's tissue. During charging of an IMD, the thermal dose should not be too large to prevent adverse effects to the patient. The term "cumulative" may be understood in such a manner that one or more thermal doses are added, i.e. cumulated. Thus, the cumulative thermal dose may be a parameter to determine a heat load of a patient's tissue more accurately (as described further below, the CEM43 may be used as cumulative thermal dose). It could, for instance, take into account at least part of the tissue temperature history, e.g. of the tissue temperature at previous times.

The control unit is configured to continue, after an interruption of the charging process and upon resumption of the charging process, determining the cumulative thermal dose based on one or more predefined conditions.

This may allow the advantage that an interruption of the charging process may not have detrimental effects upon determination of the cumulative thermal dose. This is even more pronounced if resumption after an interruption takes place. As an example, the charging process may be interrupted (accidentally) due to movements of a patient or vibrations in general. This may often be the case when an IMD is in ordinary use. Further, this may cause a variation of a relative positioning of a charging means to an IMD. Such a variation can interrupt a charging process. Similarly, such movements of a patient or vibrations in general can also lead to a resumption of the charging process (e.g. if the charging process is not finished) after an interruption. As done in conventional control means for charging, such an interruption would lead to a stop of determining a cumulative thermal dose. Furthermore, conventional control means would start again determining the cumulative thermal dose upon resumption of the charging process without acknowledging the history (e.g. from zero). However, in such conventional approaches, important information of a (cumulative) thermal dose may be lost. Said information are, however, of utmost importance to facilitate an accurate control and enable an increased health status of the patient to promote comfort, convenience and acceptance of IMD for patients. Surprisingly, the inventors found a way to overcome these deficiencies by continuing to determine the cumulative thermal dose upon resumption, if one or more predetermined conditions are met. This may also imply that the cumulative thermal dose calculation is not continued, but instead a fresh determination (from zero) is started if these one or more conditions are not met. In such an approach, the cumulative thermal dose before the interruption may be beneficially taken into consideration when continuing determining the cumulative thermal dose. Overall, this provides for an improved control system that may avoid overheated tissue as could result from prior art approaches when unintended interruptions of the charging process occur.

As used herein, to "continue determination" of the cumulative thermal dose is understood in such a way that the determination is based, at least in part, on a previously determined cumulative thermal dose. As an example, the cumulative thermal dose after interruption and upon resumption is based at least in part on the cumulative thermal dose before interruption. In some examples, the determination of the cumulative thermal load may be stopped upon interrupting the charging process and only be resumed upon resumption of the charging process (if the mentioned one or more conditions are met).

In another example, it may be possible that the determination of the cumulative thermal dose is not stopped (e.g. it may be continued) upon interruption the charging process. In such a case, it could be said that the determination of the cumulative thermal dose is continued between interruption and resumption. This may have the advantage that a thermal load and/or an increased temperature between interruption and resumption is taken into consideration.

In one example, the control unit may be configured to control the charging process based on the cumulative thermal dose. This may be appreciated by the patient as damage to the patient's tissue may be reduced, in particular during the charging process. As an example, during the charging process, the energy transfer may cause some of the energy to be converted into heat. Thus, an IMD and/or parts of the IMD may be heated up. This may not be intended. Increasing the charging power may further increase such an (unintended) heating. Even if the temperature of the IMD and/or the temperature of parts of the IMD may not reach a temperature sufficient to burn or necrose tissue adjacent to IMD, increased temperatures are generally undesirable and uncomfortable and have the potential to cause damage of the tissue. Thus, controlling the charging process based on the cumulative thermal dose has the potential to overcome these disadvantages, as the level of energy transfer can be conveniently adjusted based on the determined cumulative thermal dose. Overall, the patient's discomfort is decreased during the charging process.

As an example, controlling the charging process may comprise decreasing the duration and/or power level of the charging process, e.g. if the cumulative thermal dose is high (e.g.

higher than a predetermined threshold value). However, controlling the charging process may also comprise increasing the duration and/or the power level, e.g. if the cumulative thermal dose is low.

According to a 2nd embodiment, the control unit may be configured to send a signal to a charging means, when the cumulative thermal dose is greater than a threshold value.

A signal may be understood as any kind of means for communication, such as an electrical signal. Such a signal may be desirable, as the charging means could subsequently be controlled or could control itself based on the signal.

The threshold value may be a predefined value that is suitable for a desired area and/or tissue of the patient. Preferably the threshold value may be defined to comply with a desired area and/or tissue in proximity of the IMD, e.g. where the IMD should operate during ordinary use.

A comparison is made between the cumulative thermal dose and said threshold value.

Beneficially, such a comparison may be performed frequently to enhance the control system.

According to a 3rd embodiment, the signal is a reduction and/or termination signal.

A reduction and/or termination signal may be understood in such a manner that the signal contains information for reducing charging power and/or time and/or for terminating the charging process.

It is also appreciated that there could be a signal that is sent in case a cumulative thermal dose is lower than the threshold value. In such a manner, the signal can contain information for increasing, e.g. a charging power or charging duration.

According to a 4th embodiment, when the cumulative thermal dose is greater than a threshold value, the control unit is configured to reduce and/or to terminate communication to a charging means to reduce and/or terminate the charging process. The charging means may be a charging means as described herein.

With this arrangement, the control unit may reduce and/or terminate a communication to the charging means. This may enable the control unit to reduce and/or terminate the charging process. In such a manner, it may not be necessary that a dedicated signal, such as a termination or reduction signal, is sent. In some examples, no signal needs to be sent at all. A communication to the charging means may be understood as involving any kind of connection, preferably a wireless connection.

For example, the control unit may send a signal, e.g. on a regular and/or periodic basis. If the control unit changes a parameter of that signal, e.g. sends it less frequently, or stops sending the signal, this may indicate that the charging means shall reduce charging power or stop charging, respectively.

It is advantageous, that, when reference is made to "reducing" herein, it may comprise a stepwise reduction, a continuous reduction or any combination thereof.

According to a 5th embodiment, the cumulative thermal dose and/or the threshold value may additionally be based on a time, preferably wherein the cumulative thermal dose and/or the threshold value comprise a CEM43 parameter, such as a CEM43 according to ISO 14708-3 and/or PC76.

It is understood that the threshold value may be the threshold value of the 2nd and 4th embodiment, or any other threshold value as described herein. To be based on a time means that a time is taken into consideration when the cumulative thermal dose is determined.

CEM43 may be defined as a temperature exposure of tissue for a single minute at 43° C. In particular, CEM43 has the advantage to equate time-at-a-given-temperature and, thus, takes into account that a patient's tissue can survive for shorter periods at higher temperatures and longer durations at lower temperatures. Such principle may be reflected by way of CEM43. CEM43 may be defined according to the following equation (1):

$$CEM43 = \sum_{i}^{N} t_i \cdot R^{43-T_i}$$

Said equation may be in accordance with ISO 14708-3. In the above equation (1), $t_i$, may be the duration of the i-th time interval in minutes. The term $T_i$ may be the (average) temperature of the tissue in degrees Centigrade (also termed Celsius) during the interval $t_i$.

The term R may be a characterizing parameter and may be 0.25 for T<43° C. and/or 0.5 for T≥43° C. The term N may be the number of samples taken during the heating duration. The term R may be determined by way of experiments based on known cell and/or tissue characteristics. It is noted that R may be a different value in other examples. CEM43 may have the unit of minutes.

According to a 6th embodiment, the threshold value may be selected from the range 0.5 to 50. In some examples, CEM43 may be selected from the range 30 to 50 such as, e.g. 38 to 42, e.g. 40 for muscle/fat/peripheral nerve tissue, CEM43 may be selected from the range 10 to 30, e.g. 15 to 25, such as 21 for skin. CEM43 may be selected from the range 5 to 25, e.g. 10 to 20, such as 16 for bone. Brain tissue has a CEM43 that may be selected from the range 0.5 to 5, e.g. 2.

The threshold value in terms of CEM43 may be defined depending on the tissue at which the IMD is located or at least which is in proximity to the IMD. Thus, the threshold value may be defined in a flexible manner, which increases the health of the patient whilst the charging speed and/or charging power is maximized. In some examples, the threshold may be within the range 1 to 50, for example 35 to 45 for muscle/fat/peripheral nerve tissue.

The tissue referred to in this embodiment may be the tissue of the first aspect of the invention, e.g. it may be the tissue of the patient whose temperature may be determined by the means for determining a temperature.

As appreciated, the threshold value may be CEM43=2 minutes for brain, e.g. comparatively low. This means that merely 2 minutes at a temperature of 43° C. should prevail. This increases health of the patient as appreciated.

It is desirable to decrease the time interval (e.g. $t_i$) for determining the CEM43, which increases the accuracy to reliably determine the cumulative thermal dose, e.g. using an interval of 1 minute.

According to a 7th embodiment, the one or more predefined conditions may comprise a time limit and/or a temperature limit. Preferably, determination of the cumulative thermal dose is continued when a time span from interruption to resumption is smaller than or equal to the time limit. Additionally or alternatively, determination of the cumulative thermal dose is preferably continued when a determined temperature upon resumption is greater than or equal to the temperature limit.

Advantageously, the one or more predefined conditions can be specified in a flexible manner in order to address the needs of the IMD. The one or more predefined conditions may be important, as they aid in deciding whether the thermal load determination shall be continued to accurately reflect the actual heat load, e.g., if an inadvertent interruption of the charging process occurred. This enhances the overall charging process and contributes significantly to the comfort and health of a patient.

A time limit is advantageous, such that, based on a certain time limit, the determination of the cumulative thermal dose is continued. The time span, which may be used as a comparison to the time limit may be the time starting from an interruption of the charging process until the subsequent resumption of the charging process. If such a time span is smaller than or equal to the time limit, determination of the cumulative thermal dose may be continued, e.g., as the interruption was assessed as not intended.

A temperature limit is also beneficial. This may aid in detecting whether the temperature of the tissue is higher than usual, e.g. indicating that a charging process was or is currently performed, before an (unintended) interruption occurred. If the determined temperature is lower than the temperature limit, it may be the case that a charging process was not or is not currently performed, or a potential heating by a previous charging process has essentially cooled down again. For instance, substantially no abnormal temperature may be detected. In such a case, a continuation of determining the cumulative thermal dose may not be necessary. In an example, the determination of the cumulative thermal dose may be restarted (from zero), instead.

It is appreciated that, for determining the temperature of this embodiment, the same means as described with respect to the first aspect of the invention may be used.

Reliance on multiple predefined conditions increases the applicability of the control system. Furthermore, it enables redundancy in case of a failure of a means to determine the time span and/or the temperature. In one example, both predefined conditions should be met, e.g. fulfilled, in order for the control unit to continue the determination of the cumulative thermal dose.

According to an 8th embodiment, the time limit is selected from the range 10 minutes to 60 minutes, e.g. 10 minutes, preferably 20 minutes, more preferably 30 minutes, most preferably 60 minutes; optionally wherein the temperature limit is selected from the range 37° C. to 42° C., such as 40° C., or 39° C.

The time limit and/or the temperature could also be greater or smaller (e.g. the temperature limit could also be 41° C. or 38° C.). The advantage of a small-time limit may be that, if an intended interruption occurs, the system may quickly return to its normal state in which it may simply start determining the thermal load from zero once charging occurs or resumes. Thus, the system's complexity may be reduced and/or continuous checks for fulfillment of the predefined condition of the time limit may be avoided.

The advantage of a large time limit may particularly become apparent if the charging process is not completed, but the charging process is (accidentally) interrupted for a longer time. As an example, due to certain circumstances the charging process could be interrupted for a longer time (e.g. vibrations or movements occur that cause a relative positioning of a charging means to an IMD to vary and to maintain such a varied positioning to prevent charging). In such circumstances, the determination of the cumulative thermal dose will beneficially be continued. Thus, the history of the tissue's temperature is taken into consideration.

Thus, the inventors found that an optimal balance of the time limit should be struck, e.g. based on the values indicated herein. The time limit may depend on the tissue type and/or it may possibly also be set at least in part based on the thermal load that was reached when charging interrupted. For example, a larger time limit may be set for higher thermal loads.

Referring now to temperature, a large temperature limit has similar advantages as a small-time limit. Thus, if an intended interruption occurs, the temperature of the tissue may not need to be reduced to a large extent in order for the determination of the cumulative thermal dose not being continued (e.g. a return to a normal state). Thus, efforts for checking for compliance of the predefined condition may be reduced.

The advantage of a small temperature time limit may be similar to a large time limit. As an example, if the charging process is not completed, but the charging process is (accidentally) interrupted for a longer time, a small temperature limit may ensure that a premature resetting of the thermal load to zero is avoided.

According to a 9th embodiment, the control unit is configured to reset the determined cumulative thermal dose when a time span from interruption is greater than a time limit or when a measured temperature is lower than a temperature limit (e.g., without a resumption having occurred beforehand). The limits may be those as described above and as further outlined below. For example, the time limit may be used as a timer. If the timer lapses, the dose may be reset. Additionally or alternatively, the dose may be reset if the temperature is lower than the limit at the lapse of the timer. In other embodiments, the dose may already be reset if a temperature below the limit is measured while the timer has not elapsed.

With this embodiment, the determined cumulative thermal dose is reset, which may be understood, in one example, that the determined value is set to a reference value, such as a value of 0. This may e.g. be the case, if a charging process is, for instance, terminated by intention. For instance, if a battery is (almost) fully charged.

According to a 10th embodiment, the control unit is configured to determine the cumulative thermal dose based on a predetermined look-up table for one or more temperatures at a time period, wherein the time period is selected from the range 0.1 to 10 minutes, 0.2 minutes to 5 minutes, 0.2 minutes to 2 minutes, 0.5 minutes to 2 minutes, e.g. 0.2 minutes, 0.6 minutes, or approximately 1 minute.

With such an arrangement, a cost-effective and fast control system may be provided. In particular, such a control system may be easily implemented in a low capability microcontroller. As an example, substantially no floating-point capabilities may be required.

This is highly beneficial to reduce costs whilst at the same time providing for an accurate determination of the cumulative thermal dose. As appreciated, such an arrangement may not require performing exponential math operations to determine CEM43.

The predetermined look-up table may comprise one or more values that are associated with a time period and a temperature.

In case a temperature sensor is used as the means for determining a temperature of a tissue of a patient, the measured temperature may be used to consult the predetermined look-up table and to select a value therefrom which serves as a basis to determine the cumulative thermal dose, e.g., a CEM43. Furthermore, the values of the predetermined look-up table may form individual terms. Thus, to retrieve the cumulative sum, the values could be added each time the predefined look-up table is consulted.

According to another embodiment, the means for measuring a temperature is a temperature sensor.

Optionally, the control unit is an onboard controller. As an example, onboard may be understood as a hardware component embedded into a circuit board. However, the control unit is not limited thereto. The control unit may be an onboard microcontroller, application-specific integrated circuit, ASIC, or a custom chip, etc.

According to an 11th embodiment, the means for measuring the temperature is in thermal contact with an IMD, e.g. an implantable pulse generator, IPG, e.g. a can of the IPG.

Thermal contact may be established by a material to minimize a thermal impedance of the means for measuring a temperature and the IPG can.

In a further example, the means for measuring the temperature may not be in thermal contact with an IMD, such as an IPG (can).

An IPG may be understood as a part comprising metal objects, wherein eddy currents may be induced in the metal parts of the IPG, when a battery of the IMD is charged. Further, an IPG may be an electrical source that causes current to flow through an extension and lead wires to an electrode, across the electrode-tissue interface, and back through the tissue to an IPG can, which may be the return electrode. An IPG can operate as either a current source or a voltage source.

A second aspect of the invention is related to a system comprising an implantable medical device, IMD or an external charging means for charging an implantable medical device, IMD. The system may further comprise a control system according to any one of the embodiments and/or aspects outlined herein. The control system may be comprised by the IMD or the external charging means.

All aspects and/or embodiments described with reference to the control system of the first aspect (or other aspects) are also applicable to the control system as referred to in the second aspect.

As an example, the means for determining a temperature could be part of or integral with the external charging means. For instance, the means could monitor a power level transferred to the IMD and based thereon, estimate a temperature of the tissue of a patient. The means may also be configured to sense the skin temperature of a patient and/or it may be configured to be in contact with a skin of a patient.

In another example, the means for determining a temperature could be a part of or integral with the IMD, e.g. for being in contact with a tissue of a patient.

In some examples, means for determining a temperature may be provided in an IMD and in a corresponding charging means. Hence, charging may be controlled based on tissue temperature and skin temperature, for example.

According to a 13th embodiment, the external charging means may be configured to receive a signal based on the cumulative thermal dose of a patient (e.g. as determined by the control system, e.g. in the IMD). The IMD may comprise means for receiving a charging power during the charging process of the IMD (e.g. as sent from the external charging means).

A third aspect of the invention is related to a method for controlling a charging process of an implantable medical device, IMD, for a patient, the method comprising charging an IMD. The method may further comprise determining, during charging, a temperature of a tissue of a patient. Moreover, the method may comprise determining, using the determined temperature, a cumulative thermal dose of the patient. Furthermore, the method may comprise continuing the determination of the cumulative thermal dose, after an interruption of charging and upon resumption of charging, based on one or more predefined conditions, wherein the determined cumulative thermal dose is reset when a time span from interruption is greater than a time limit and/or when a measured temperature is lower than a temperature limit.

Optionally, the third aspect may comprise controlling, using the cumulative thermal dose, charging of the IMD.

The step of determining a temperature of a tissue of a patient may advantageously be performed during the charging process. However, such a determination may also be performed, if e.g. a charging process is interrupted. In another example, such a determination may also be performed if substantially no charging process is performed.

It is noted that the method steps as described herein may include all aspects and/or embodiments described herein, even if not expressly described as method steps but rather with reference to a system (or device or apparatus). It is also to be understood that the features and advantages described with reference to an apparatus (or device or system) may equally be applicable to the method steps. Moreover, the system (or device or apparatus) as outlined herein may include means for implementing all aspects and/or embodiments as outlined herein, even if these may rather be described in the context of method steps. Furthermore, the features and advantages described with reference to the method steps may equally be applicable to the system (or device or apparatus).

A fourth aspect of the invention is related to a computer program comprising instructions which, when the program is executed by a computer, cause the computer to carry out one or more steps of the methods described herein.

Whether described as method steps, computer program and/or means, the functions described herein may be implemented in hardware, software, firmware, and/or combinations thereof. If implemented in software/firmware, the functions may be stored on or transmitted as one or more instructions or code on a computer-readable medium.

Computer-readable media include both computer storage media and communication media including any medium that facilitates transfer of a computer program from one place to another. A storage medium may be any available media that can be accessed by a general purpose or special purpose computer. By way of example, and not limitation, such computer-readable storage media can comprise RAM, ROM, EEPROM, FPGA, CD/DVD or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor.

The control unit as described herein may also be implemented in hardware, software, firmware, and/or combinations thereof, for example, by means of one or more general-purpose or special-purpose computers, and/or a general-purpose or special-purpose processors.

In the following, preferred embodiments are described, by way of example only. Reference is made to the following accompanying figures:

FIG. 1 Schematic representation of an exemplary embodiment of a control system according to the present invention.

Figure 2:
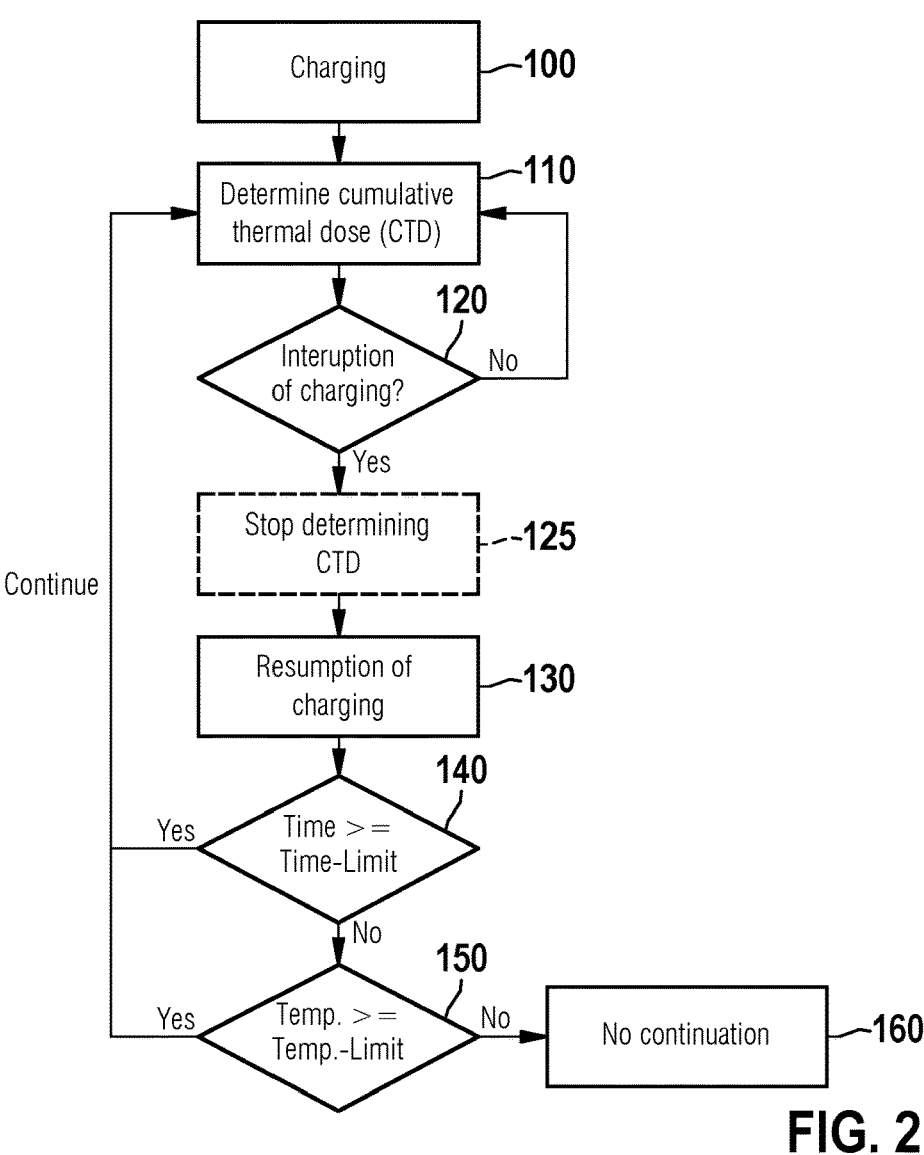

FIG. 2 Schematic representation of a flow diagram that illustrates an example of a control system according to the present invention.

Figures 3, 4:
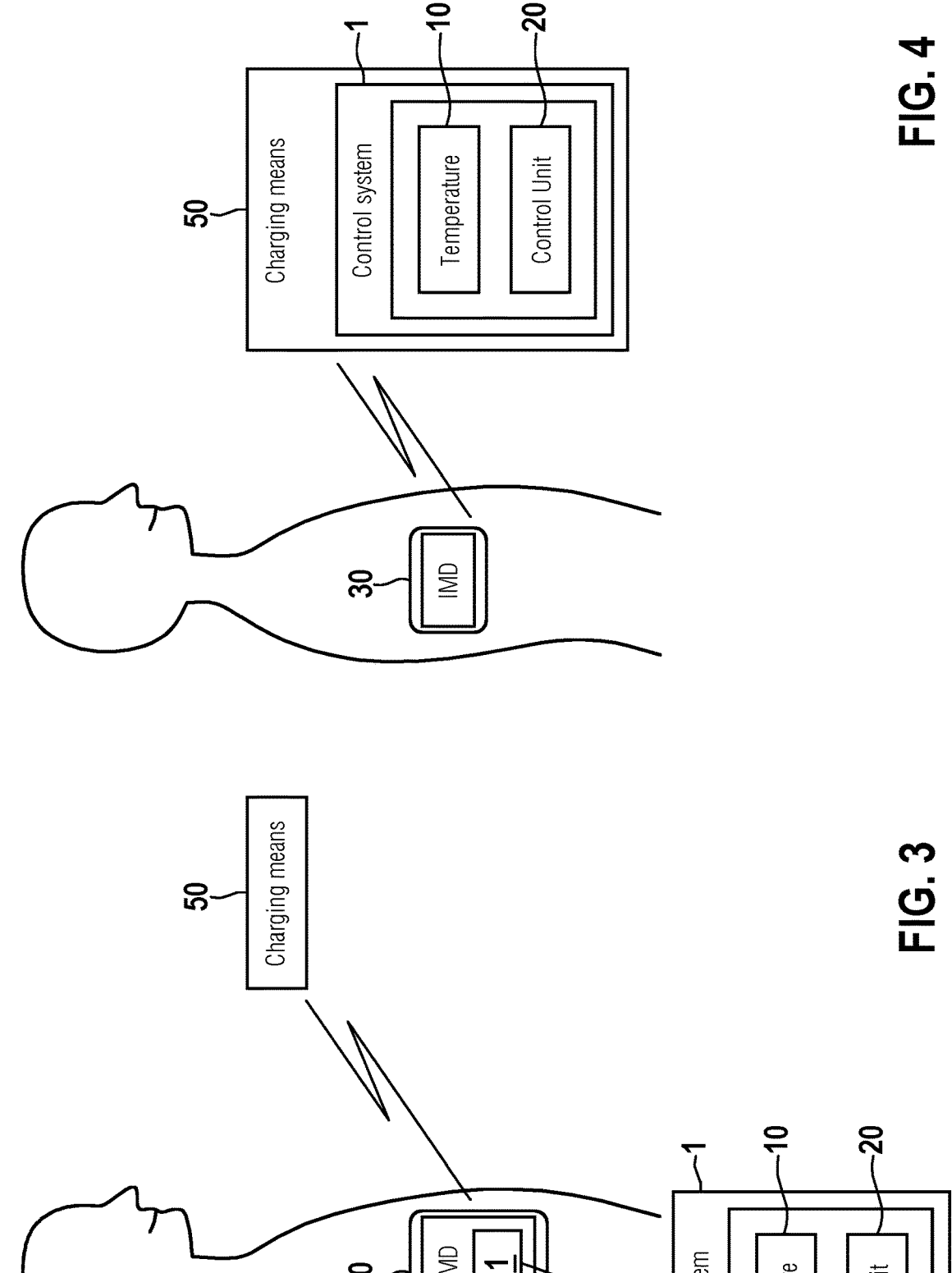

FIG. 3 Schematic representation of an exemplary embodiment of a system comprising an IMD and a control system comprised by the IMD, the IMD being charged by a charging means.

FIG. 4 Schematic representation of an exemplary embodiment of a system comprising an external charging means for charging an IMD and a control system comprised by the external charging means, the external charging means being configured to receive a signal based on the cumulative thermal dose of a patient.

Figure 5:
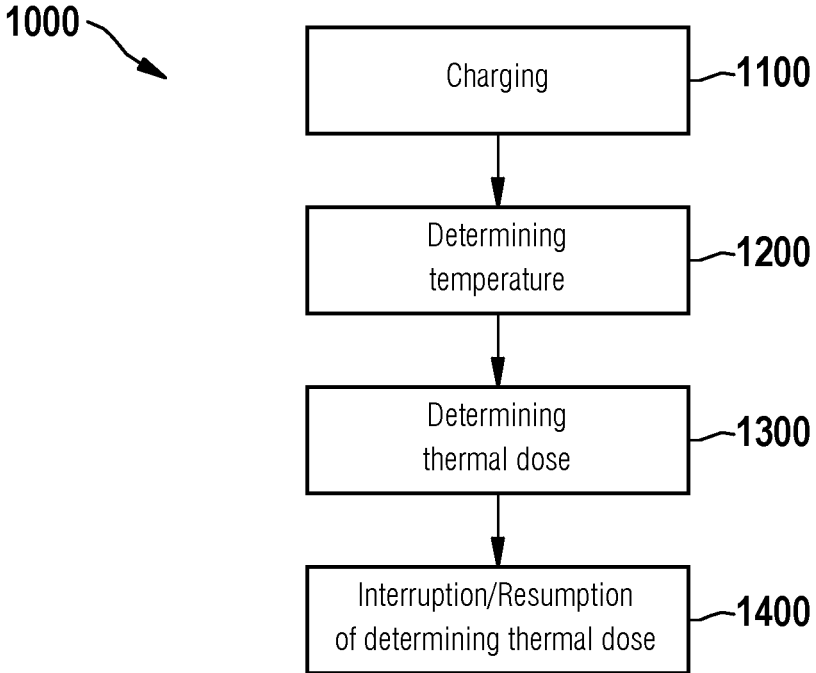

FIG. 5 Schematic representation of a flow chart that illustrates an example of a method for controlling a charging process according to the present invention.

In the subsequent passages, the invention is described with reference to the accompanying figures in more detail. It is noted that further embodiments are certainly possible, and the below explanations are provided by way of example only, without limitation.

While specific feature combinations are described with respect to the exemplary embodiments of the present invention, it is to be understood that not all features of the discussed embodiments have to be present for realizing the invention, which is defined by the subject matter of the claims. The disclosed embodiments may be modified by combining certain features of one embodiment with one or more features of another embodiment. Specifically, the skilled person will understand that features, components and/or functional elements of one embodiment can be combined with technically compatible features, components and/or functional elements of any other embodiment of the present invention given that the resulting combination falls within the definition of the invention provided by the claims. The skilled person also understands that certain features may be omitted in so far as they appear dispensable.

Throughout the present figures and specification, the same reference numerals refer to the same elements. The figures may not be to scale, and the relative size, proportions, and depiction of elements in the figures may be exaggerated for clarity, illustration, and convenience.

FIG. 1 shows a schematic representation of an exemplary embodiment of a control system 1 according to the present invention. The control system 1 is suited for controlling a charging process of an implantable medical device, IMD, 30 for a patient. The control system 1 comprises means for determining a temperature 10 of a tissue of a patient. The control system further comprises a control unit 20, which is configured to determine a cumulative thermal dose of the patient based on the determined temperature. Furthermore, the control unit 20 is configured to continue, after an interruption of the charging process and upon resumption of the charging process, the determination of the cumulative thermal dose based on one or more predefined conditions.

As further detailed below, the one or more predefined conditions may comprise a time limit and/or a temperature limit.

The cumulative thermal dose may typically be based on a time, and one or more corresponding thresholds may be used for controlling charging based on the dose. As an example, the cumulative thermal dose may comprise a CEM43 parameter. The CEM43 may be a normalizing method to convert the various time-temperature exposures applied into an equivalent exposure time expressed as minutes at a reference temperature of 43° C. Stated in other words, the CEM43 may be referred to as the cumulative equivalent minutes at 43° C. for constant temperature intervals. One or more thresholds may be defined and e.g. stored in the control system, wherein charging may be reduced or stopped when the corresponding threshold is reached.

The following table shows exemplary upper limits for CEM43 depending on the tissue type:

| Tissue | CEM43 dose threshold |
|---|---|
| muscle | 40 |
| fat | 40 |
| peripheral nerve | 40 |
| skin | 21 |
| bone | 16 |
| brain | 2 |
| BBB (blood brain barrier) | 15 |

The numerical values in the above table serve merely as examples and are not intended to limit the scope of the present invention. However, as an example, a CEM43 threshold of 40 (minutes) may be set in tissue of muscle/fat, for example. CEM43=20 minutes may be set on skin.

FIG. 2 shows a schematic representation of a flow diagram that illustrates an exemplary operation of a control system according to the present invention. This figure particularly describes the one or more predefined conditions may comprise a time limit and/or a temperature limit.

Step 100: a charging process 100 may be started or may be running (termed charging 100 for brevity in this figure). For instance, an IMD may be charged, wherein the IMD is located in proximity of a patient's tissue. The IMD may employ a rechargeable battery, which requires recharging. Typically, such a recharging could be performed by using inductive or resonant magnet wireless power transfer (WPT). The charging may be performed with the aid of a charging device. As an example, an external charging device may be employed.

Step 110: during charging 100 a cumulative thermal dose, CTD, (such as the CEM43) may be determined 110. Based on the determined CTD, the charging process is controlled, e.g. more or less charging power may be adjusted, depending on the CTD and a threshold value. Such threshold value should be set according to the tissue in proximity of the IMD. It is to be noted that FIG. 2 may not explicitly outline details of the controlling of the charging process based on the CTD. However, this does not mean that the exemplary flow chart is limited by any means. In contrast, the exemplary flow chart is compatible and can be combined with the remaining embodiments and aspects of this invention.

Step 120: a check may be performed, whether an interruption of the charging process has occurred. This may be the case, when, during a charging process, such charging stops. As an example for a cause of such an interruption, movements of a patient or vibrations in general may be mentioned. Such movements or vibrations may cause a relative positioning of a charging means to an IMD to vary, which can interrupt a charging process. For example, this step 120 may be carried out periodically.

Step 125: in a subsequent optional step of the exemplary flow chart, the determination of the cumulative thermal dose is stopped after an interruption of the charging process. In such a manner, the exposure of the patient's tissue to a temperature may not be taken into consideration for the CTD. In other words, the value that the CTD had before the interruption is maintained, e.g. kept.

In some examples, step 125 is omitted, and CTD determination is continued.

Step 130: to illustrate the one or more predefined conditions, step 130 indicates that a resumption of the charging process occurs. Analogously to an interruption of charging, movements of a patient or vibrations can also lead to a resumption of the charging process. This may be even more pronounced if the charging process is not finished. The control system may detect charging, for example.

Step 140: in this step, the time span from interruption to resumption is compared with a time limit, which may be predefined. In this case, the time limit may also be referred to as an upper time limit because the condition is fulfilled if the time span is lower or equal to the upper time limit. The time limit may be about 10, 20, 30 or 60 minutes or any other suitable time limit. If this condition is fulfilled, determination of the cumulative thermal dose (step 110) is continued.

Step 150: in this step, the temperature (indicated as Temp. for brevity) is checked. This step may represent a predefined condition (additional or alternative to that of step 140) that needs to be fulfilled for continuing the determination of the cumulative thermal dose upon resumption of the charging process (step 130). The temperature (Temp.) may be a current temperature of the patient's tissue, such current temperature may be determined, e.g. it could be measured using one or more temperature sensors, or it could be determined using a (numerical) model. Employing more than one temperature sensor may be beneficial to increase an accuracy of the measured temperature. The check of the temperature may aid in detecting whether the temperature of the tissue is higher than usual. Thus, one could deduce that a charging process was or is currently performed, before an (unintended) interruption occurred. If the determined temperature is lower than the temperature limit, it may be the case that a charging process was not or is not currently performed. In this case, the temperature limit may also be referred to as a lower temperature limit because the condition is fulfilled if the temperature is greater than or equal to the temperature limit. The temperature limit may be 40° C., or 39° C. or any other suitable temperature limit depending on the patient's tissue in proximity of the IMD. If this condition is fulfilled, determination of the cumulative thermal dose (step 110) is continued.

As shown in the example of FIG. 2, if either of tests 140 or 150 is fulfilled, CTD determination is continued. Notably, their order could also be exchanged or one of the tests could be omitted.

Continuation of determining the CTD upon resumption of charging after an (unintended) interruption of charging has the advantage that said interruption of the charging may not have adverse effects upon determination of the cumulative thermal dose. Thus, upon resumption, the history of the tissue's thermal load is accurately taken into account. This culminates in a greater comfort and a reduced health risk of the patient during a charging process. In particular, the above outlined schematic representation of a flow diagram may aid in reaching a full potential of the advantageous effects of controlling a charging process, which cannot be achieved according to conventional approaches.

Step 160: If the one or more predefined conditions (step 140 and step 150) are not fulfilled, there is not continuation in determining the CTD. For instance, this may be the case, if the resumption (step 130) takes place several days after an (intended) interruption. As an example, this could occur, when an ordinary charging process is completed.

As appreciated, the above-mentioned steps may be repeated so as to beneficially participate from the advantages of the control system, any time an interruption and resumption of charging may occur.

In some examples, steps 140 and 150 may be omitted. Instead, after step 120 (and optional step 125) a timer may be set and/or temperature may be determined repeatedly. If either the timer lapses or the temperature is below a temperature limit, the CTD may be reset (e.g. to zero). If charging resumes at step 130 before either condition is met, CTD determination is resumed. If charging resumes at step 130 after one of the conditions is met, CTD starts anew (e.g. from zero).

FIG. 3 shows a schematic representation of an exemplary embodiment of a system comprising an IMD 30 and a control system 1 comprised by the IMD, the IMD being charged by a charging means 50. The IMD may be located in proximity of a patient's tissue, as indicated in this figure. As an example, the IMD may be located close to the patient's spine. A multitude of applications of IMD and positions within a patient's body are possible, such as cages, hooks, plates, screws, rods, and spinal cord stimulators.

The IMD may further comprise a means for receiving a charging power during the charging process of the IMD. The means for receiving a charging power may comprise a battery. In particular, the IMD may employ one or more batteries, e.g. rechargeable batteries. The one or more batteries can require a periodic form of recharging. Recharging may employ inductive or resonant magnetic wireless power transfer (WPT). In this manner, eddy currents may be induced in metal parts of an Implantable Pulse Generator (IPG), causing the metal parts, the IPG and/or the IMD to heat up.

Primarily, such a charging as envisaged herein may be directed to wireless transfer of energy between two coils. This may be termed inductive coupling. Still, it may also be possible to transfer energy for charging by employing a physical connection between a (potentially external) charging means and a rechargeable power supply (comprised by the IMD).

As indicated in FIG. 3, the control system 1 comprises means for determining a temperature 10 of a tissue of a patient and a control unit 20 as described herein. The means for determining a temperature 10 may be a temperature sensor and may be integral with the IMD for being in contact with a tissue of a patient. In other examples, additionally or alternatively, a means for determining a temperature may be comprised by the charging means 50.

A signal may be sent by the control unit 20 to the charging means 50. The signal could be a reduction and/or termination signal. For instance, such a signal could be sent, when a cumulative thermal dose is greater or equal than a threshold value. In such a case, a charging power should be reduced or terminated. Thus, an overheating and/or discomfort of the patient's tissue (during a charging process) is advantageously alleviated.

FIG. 4 shows a schematic representation of an exemplary embodiment of a system comprising an external charging means 50 for charging an IMD 30 and a control system 1 comprised by the external charging means 50. As an example, the IMD may be located close to the patient's spine. A multitude of applications of IMD are possible, such as pacemakers, defibrillators, pressure sensors, neurostimulators, or the like. The external charging means 50 is external, which could mean that the charging means 50 is not within the patient's body. But it could also be in the body, e.g. close to the surface of the body and merely be external to the IMD.

It is noted that the control system 1 comprises means for determining a temperature 10 of a tissue of a patient and a control unit 20 as described herein. The external charging means 50 may be configured to receive a signal based on the cumulative thermal dose of a patient.

The external charging means 50 may also comprise one or more features as described with reference to FIG. 4. Thus, a wireless charging and a charging including physical connection may be possible.

The received signal may comprise a reduction and/or termination signal. Such a signal may be sent by the control system 1. For instance, such a signal could indicate that a cumulative thermal dose is greater or equal than a threshold value, such that a charging power should be reduced or terminated. Thus, an overheating and/or discomfort of the patient's tissue, preferably during a charging process, is advantageously alleviated.

In some examples, means for determining temperature may additionally or alternatively be provided in the IMD.

It is to be noted that the examples in the previous figures (in particular the two preceding figures) participate on an improved, e.g. more realistic and reliable, determination of a cumulative thermal dose, which takes into account any potential use cases that comprise an interruption and resumption of the charging process.

FIG. 5 shows a schematic representation of a flow chart that illustrates an example of a method 1000 for controlling a charging process according to the present invention.

The method 1000 comprises the step of charging an IMD 1100. Furthermore, the method 1000 comprises the step of determining 1200, during charging, a temperature of a tissue of a patient. Moreover, the method 1000 comprises determining 1300, using the determined temperature, a cumulative thermal dose of the patient.

In addition, the method 1000 comprises continuing, after an interruption of charging and upon resumption of charging, the determination 1400 of the cumulative thermal dose based on one or more predefined conditions.

It is to be noted that the one or more predefined conditions may be any one as described herein, reference is made for instance to the one or more predefined conditions as described in FIG. 2 above.

The method 1000 may also control, using the cumulative thermal dose, charging of the IMD.

REFERENCE NUMERALS

1 control system
10 means for determining (a temperature)
20 control unit
30 implantable medical device
50 charging means
100 charging
110 determining cumulative thermal dose
120 check for interruption of charging
125 stop determining cumulative thermal dose
130 resumption of charging
140 check for time limit
150 check for temperature limit
160 no continuation
1000 method for controlling a charging process
1100 charging an IMD
1200 determining a temperature of a tissue of a patient
1300 determining a cumulative thermal dose of the patient
1400 continuing (after an interruption of charging and upon resumption of charging) the determination of the cumulative thermal dose

The invention claimed is:

1. A control system (1) for controlling a charging process of an implantable medical device, IMD, for a patient, the control system (1) comprising:
means for determining a temperature (10) of a tissue of a patient;
a control unit (20) configured to determine and set a cumulative thermal dose of the patient based on the determined temperature;
wherein the control unit (20) is configured to continue, after an interruption of the charging process and upon resumption of the charging process, the determination of the cumulative thermal dose based on one or more predefined conditions,
wherein the control unit (20) is configured to reset the determined cumulative thermal dose to a reference value when a time span from interruption is greater than a time limit and/or when a measured temperature is lower than a temperature limit.

2. The control system (1) according to claim 1, wherein the control unit (20) is configured to send a signal to a charging means (50), when the cumulative thermal dose is greater than a threshold value.

3. The control system (1) according to claim 2, wherein the signal is any of a reduction and a termination signal.

4. The control system (1) according to claim 2, wherein the cumulative thermal dose and/or the threshold value is additionally based on a time, preferably wherein the cumulative thermal dose and/or the threshold value are/is a CEM43 parameter, such as a CEM43 according to ISO 14708-3 and/or PC76.

5. The control system (1) according to claim 2, wherein the threshold value is selected
from the range CEM43=30 to CEM43=50 if the tissue is muscle/fat/peripheral nerve tissue; and/or
from the range CEM43=10 to CEM43=30 if the tissue is skin; and/or from the range CEM43=5 to CEM43=25 if the tissue is bone tissue; and/or
from the range CEM43=0.5 to CEM43=5 if the tissue is brain tissue.

6. The control system (1) according to claim 1, wherein, when the cumulative thermal dose is greater than a threshold value, the control unit (20) is configured to reduce and/or to terminate communication to a charging means (50) to reduce and/or terminate the charging process.

7. The control system (1) according to claim 1, wherein the one or more predefined conditions comprise a time limit and/or a temperature limit, wherein determination of the cumulative thermal dose is preferably continued
when a time span from interruption to resumption is smaller than or equal to the time limit, and/or
when a determined temperature upon resumption is greater than or equal to the temperature limit.

8. The control system (1) according to claim 7, wherein the time limit is 10 minutes, 20 minutes, 30 minutes, or 60 minutes.

9. The control system (1) according to claim 7, wherein the temperature limit is 40° C. or 39° C.

10. The control system (1) according to claim 1, wherein the control unit (20) is configured to determine and set the cumulative thermal dose based on a predetermined look-up table for one or more temperatures at a time period, wherein the time period is selected from the range 0.2 minutes to 5 minutes, 0.5 minutes to 2 minutes, or approximately 1 minute.

11. The control system (1) according to claim 1, wherein the means for measuring the temperature is in thermal contact with an implantable pulse generator, IPG.

12. A system comprising:
an implantable medical device, IMD, and/or an external charging means (50) for charging an IMD;
a control system (1) according claim 1 comprised by the IMD or the external charging system.

13. The system according to claim 12,
wherein the external charging means (50) is configured to receive a signal based on the cumulative thermal dose of a patient.

14. The system according to claim 12, wherein the IMD further comprises a means for receiving a charging power during the charging process of the IMD.

15. The control system (1) according to claim 1, wherein the reference value is zero.

16. A method for controlling a charging process of an implantable medical device, IMD, for a patient, the method comprising:
charging an IMD;
determining, during charging, a temperature of a tissue of the patient;
determining and setting, using the determined temperature, a cumulative thermal dose of the patient;
wherein, after an interruption of charging and upon resumption of charging, the determination of the cumulative thermal dose is continued based on one or more predefined conditions,
wherein the cumulative thermal dose is reset to a reference value when a time span from interruption is greater than a time limit and/or when a measured temperature is lower than a temperature limit.

17. A computer program comprising instructions which, when the program is executed by a computer, cause the computer to carry out the method of the preceding claim 16.

18. The method of claim 16, wherein the reference value is zero.

19. A control system (1) for controlling a charging process of an implantable medical device (IMD), the control system comprising:

a processor; and a memory storing instructions that, when executed by the processor, cause the processor to:

determine and set a cumulative thermal dose of a patient based on a temperature of a tissue of the patient, continue, after an interruption of the charging process and upon resumption of the charging process, the determination of the cumulative thermal dose based on one or more predefined conditions, and reset the cumulative thermal dose to a reference value when a time span from the interruption is greater than a time limit and/or when a measured temperature is lower than a temperature limit.

20. The control system of claim 19, wherein the reference value is zero.

* * * * *